United States Patent [19]

Schaupp et al.

[11] Patent Number: 5,496,818
[45] Date of Patent: Mar. 5, 1996

[54] STABLE EMULSION SUITABLE FOR PHARMACEUTICAL ADMINISTRATION, THE PRODUCTION THEREOF AND EMULSION FOR PHARMACEUTICAL USE

[75] Inventors: Karin Schaupp; Josef Polzer; Johannes Kerbl, all of Graz; Kurt Lanthaler, Poels, all of Austria; Stanley S. Davis; Clive Washington, both of Nottingham, Great Britain

[73] Assignee: Knoll Aktiengesellschaft, Ludwigshafen, Germany

[21] Appl. No.: 57,553

[22] Filed: May 6, 1993

Related U.S. Application Data

[62] Division of Ser. No. 697,035, May 8, 1991, abandoned.

[30] Foreign Application Priority Data

May 11, 1990 [DE] Germany .......................... 40 15 108.5

[51] Int. Cl.$^6$ .......................... A61K 31/54; A61K 31/275
[52] U.S. Cl. .................................... 514/225.8; 514/226.2; 514/523; 514/786; 514/224.8
[58] Field of Search ...................... 514/786, 523, 514/226.2, 224.8, 225.8

[56] References Cited

U.S. PATENT DOCUMENTS

| | | | |
|---|---|---|---|
| 4,777,183 | 10/1988 | Lenke et al. | 514/523 |
| 4,816,247 | 3/1989 | Desai et al. | 424/80 |
| 4,880,634 | 11/1989 | Speiser | 424/450 |
| 5,364,632 | 11/1994 | Benita et al. | 424/450 |

*Primary Examiner*—Richard L. Raymond
*Assistant Examiner*—Mary C. Cebulak
*Attorney, Agent, or Firm*—Keil & Weinkauf

[57] ABSTRACT

A stable active substance emulsion of the oil-in-water type with a phospholipid as emulsifier is described, where the active substance dissolved in the lipid phase has one or more basic groups, is hydrophobic and oil-soluble, and has a pKa of at least 7.5, the aqueous phase is set at an acid pH, and the disperse phase gives a positive zeta potential of at least +15, but preferably +30, mV after dilution of the emulsion ready for administration to a fat content of 0.08% by weight.

7 Claims, 1 Drawing Sheet

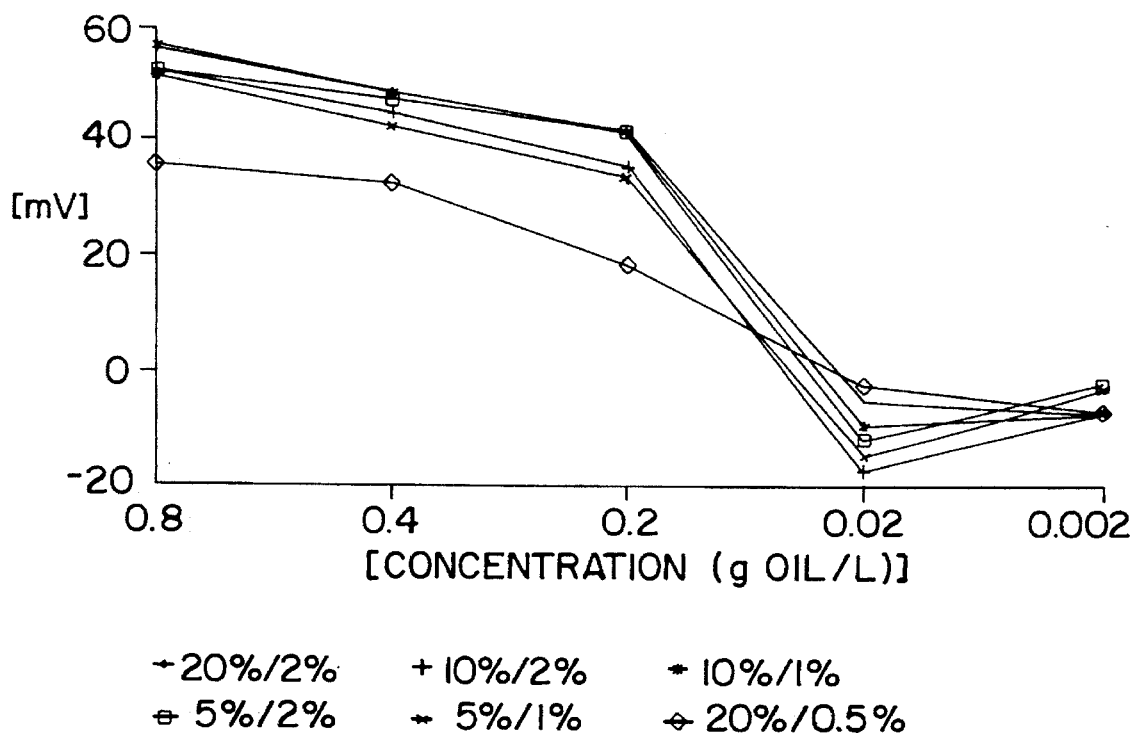

STABLE EMULSION SUITABLE FOR PHARMACEUTICAL ADMINISTRATION, THE PRODUCTION THEREOF AND EMULSION FOR PHARMACEUTICAL USE

This is a division of application Ser. No. 07/697,035, filed May 8, 1991, now abandoned.

The present invention relates to an emulsion of the oil-in-water type which contains a hydrophobic basic active substance dissolved in the oil phase. It is suitable for pharmaceutical, especially intravenous, administration and has very high stability which is based on an electrostatic repulsion of the disperse phase.

DE-B 1 792 410 discloses that pharmaceutical compositions in which the active substance to be administered is finely dispersed or, in particular, dissolved in the hydrophobic phase of a system of the lipid-in-water type, are particularly well suited for intravenous administration and are often distinguished from aqueous presentations of the same active substance by being better tolerated and having fewer side effects. In many cases, an increase in activity has also been observed with these compositions. Used to stabilize the lipid-in-water system acting as carrier in this case are stabilizing substances of natural or synthetic origin such as phosphatides, polypropylene/polyethylene glycol, polyglycerol monooleate, and the amount thereof employed depends, according to the description, on the particular properties of the system. Used in the examples is a mixture of phosphatides, such as egg phosphatide, with nonionic emulsifiers, e.g. polyoxyethylene which is partially esterified with stearic acid, where 1–2% by weight of phosphatide are employed together with about 0.5% by weight of the nonionic emulsifier in 10% oil-in-water emulsions.

In contrast to the emulsions of DE-B 1 792 410 in which no organic solvents are used there are also proposals for the production of presentations for hydrophobic active substances in the form of fat emulsions in which organic solvents are employed as auxiliaries. Thus, U.S. Pat. No. 4,784,845 proposes the use of benzyl alcohol as cosolvent for producing fat emulsions of, inter alia, those basic active substances whose pKa is below or near physiological pH, and which are therefore only very weakly basic, and DE-A 3 702 029 recommends the use of isopropanol for producing fat emulsions with, inter alia, 2-dodecyl-5-(methyl-3-methoxyphenethylamino)-2-(3-methoxyphenyl)valeronitrile (anipamil) as active substance by means of a complicated process, in which case this solvent is removed, at the same time as most of the water, from the system only after addition of a protective colloid such as gelatin.

The resulting concentrate then contains only small amounts of water and is no longer a lipid-in-water emulsion within the meaning of the present invention.

Such emulsions containing organic solvents are preferable to emulsions which comprise only an oil-in-water emulsion with a solvent-free aqueous phase and phospholipids as emulsifier, especially when they are administered intravenously, because the latter are similar to chylomicrons which carry out the physiological transport of fats in the blood and which contain phospholipids in the membrane (see DE-B 1 792 410). They are therefore more acceptable from the physiological standpoint.

It is likewise emphasized by Davis, S. S. et al., Ann. New York Acad. Sci. 507 (1987) 76–79, who point out therein the importance which has been acquired by emulsions of the oil-in-water type as form for the administration of oil-soluble but not water-soluble pharmaceutical active substances, that such emulsions, which are usually composed of 10–20% by volume of a vegetable oil which is stabilized by 1–2% by weight of phosphatides, are similar to chylomicrons and are superior to systems based on organic solvents and synthetic surfactants such as Cremophor, because their intravenous tolerability is better.

These emulsions also have a certain similarity to liposomes, but differ from the latter, according to Davis, S. S. et al., by being more easily produced in a well-tested manner and having good storage stability. It is an advantage that such fat emulsions can also be used as presentation for those active substances which are unstable in aqueous medium or show undesired side effects in aqueous presentations. On the other hand, it is regarded as a disadvantage that some active substances crucially impair the stability of the basic emulsion or even destroy the emulsion. No reason for the adverse effect of some active substances is given.

S. S. Davis has also pointed out, in Adv. Clin. Nutrition—Proc. 2nd Int. Symp. Editio I. D. A. Johnston 1982, pages 213–239, that the stabilizing effect of emulsifiers can be both mechanical and electrical in nature, the mechanical stabilization being based on the formation of a thick film at the interface, and the electrical stabilization being based on an electrostatic repulsion of the droplets of the disperse phase by a charge of the same type at the interface. Employed for parenteral administration are primarily fat emulsions with lecithin of animal or vegetable origin as emulsifier, which, because of additions of small amounts of acid such as phosphatidic acid, phosphatidylserine and similar substances, confer on the fat droplets a negative charge which is crucial for the stability of such emulsions. These electrostatic forces may be expressed by the zeta potential of the fat droplets which is, according to Römpps Chemie Lexikon, Otto Albrecht Neumüller—Stuttgart: Franckh, Vol. 6, 8th edition, page 4695, the potential of the particles which acts outwards and is responsible for their electrokinetic phenomena and is therefore also called electrokinetic potential. The stability of the emulsion increases with the size of the negative zeta potential.

Davis also points out that addition of cations reduces the negative zeta potential of the fat emulsions, which is at from −40 to −50 mV in commercial fat emulsions, and thus leads to instability of the emulsion. In the case of singly charged cations such as sodium or potassium ions, addition of more than 130 mmol/l destroys the emulsion, and in the case of doubly or triply charged cations the destructive effect occurs at considerably lower concentrations. Addition of multiply charged cations may even result in complete discharge of the fat droplets or a change in charge to a positive zeta potential.

The present invention is based on the finding that it is usually basic active substances which cause the instability of fat emulsions intended to act as carriers for these active substances. This destabilizing effect increases with the pKa of the basic active substance. Thus, it is true that it is possible to produce stable pharmaceutical compositions based on fat emulsions with weakly basic active substances, such as diazepam, or weakly acid active substances, such as propofol, and it has emerged that this is connected with there being little or no change owing to the addition of the said active substances in the negative zeta potential of the fat emulsion forming the basis. On the other hand, it has been found, surprisingly, that with more strongly basic active substances, especially those with a pKa of 8 or above, the positive ionization of the active substance at pH 7 may, despite its insolubility in water, suffice in a 10% strength soybean oil emulsion virtually to neutralize the negative charge at the interface of the fat droplets or even to bring about a certain change in charge and thus eliminate the electrostatic repulsion which has a stabilizing effect. Thus, for example, in the case of the known calcium antagonist (−)-(S)-2-isopropyl- 5-(methylphenethylamino)-2-phenylvaleronitrile (levemopamil), which is extremely hydrophobic [partition coefficient (octanol/water, non-ionized) log P 6–7, determined by calculation] and has a pKa of 8.58, it has emerged that the ionized proportion of 2% in an emulsion containing 10% soybean oil suffices to change the zeta potential of the emulsion, which is −40 mV with no active substance present, to −10 to +5 mV at pH 7, which is the reason for the instability of the pharmaceutical composition with this active substance.

We have now found, surprisingly, that hydrophobic, strongly basic active substances can be formulated to stable pharmaceutical compositions based on an oil-in-water emulsion stabilized with phospholipid when an acidic pH which is sufficient to bring about a change in charge to a highly positive zeta potential is set up in the aqueous phase by addition of a buffer system. The setting up of an acid pH in the aqueous phase, for example to pH 6 or below, increases the ionization of the active substance which is sparingly soluble in water to such an extent that the zeta potential of the disperse phase is shifted, while maintaining the solubility in oil, so far into the positive range that the repulsive forces of the now positively charged fat droplets suffice to stabilize the emulsion. This is surprising because this effect occurs even at relatively low concentrations of active substance based on the complete system. Thus, for example, in the case of levemopamil 2% of active substance, based on the complete system, which is 60 mmol/l, of which only a fraction is ionized, suffices to give a positive zeta potential of about +35 to +40 mV at pH 6. The zeta potential can even be increased to above +50 mV by setting up a pH of 5.

Naturally, the electrostatic conditions in the emulsion ready for administration are crucial for the occurrence of the stabilizing effect. However, it has emerged in practice that it is not possible to measure the zeta potential, for example by measurement of the rate of migration by microelectrophoresis, coupled with a laser Doppler velocimetry, in these emulsions which contain 5–30% by weight fat, because the transparency of these emulsions is too low. On the other hand, there is in the present case the difficulty that the positive zeta potential resulting in the finished composition is not attributable to the presence of foreign electrolytes in the aqueous phase, on the contrary these electrolytes are formed by the active substance which is present in the oil phase undergoing ionization, which is increased by dilution of the sample. The effect of the dilution necessary for measurement is so serious in this connection that, as our investigations have shown, emulsions whose zeta potential is approximately in the range from +40 to +60 mV reach the zero point or even slip into negative values with dilutions of from 1:4,000 to 1:10,000. However, it has emerged that zeta potentials can be measured at fat concentrations of 0.08% by weight using commercial laser electrophoresis and submicron particle size distribution analyzers, and the results correlate very well with those of the undiluted emulsion, as is evident from the dilution plot. In this connection, see FIG. 1, change in zeta potentials of dilutions containing from 0.08% by weight to 0.0002% by weight of oil. If measurement of a 0.08% by weight emulsion reveals a positive zeta potential of at least +15 mV, it has emerged that the stable range for this emulsion has been reached, and it is advisable to prepare emulsions which, on measurement of the composition ready for administration which has been diluted to a fat content of 0.08% by weight, have a zeta potential of at least +30 mV, preferably of at least +40 mV, to ensure long-term stability and autoclavability at 120° C.

These emulsions containing 0.08% by weight fat are obtained, for example, when an originally 20% by weight fat emulsion is diluted 250 fold,
10% by weight fat emulsion is diluted 125 fold and
5% by weight fat emulsion is diluted 62.5 fold.

Thus, all the positive zeta potentials stated in the following description were deter-mined on emulsions containing 0.08% by weight fat.

Accordingly, the present invention relates to stable emulsions which are suitable for pharmaceutical, especially intravenous, administration of the oil-in-water type with a fat content of 5–30 % by weight and a content of 0.5–2% by weight of a phospholipid as emulsifier, and which contain in the lipid phase a hydrophobic pharmaceutical active substance carrying one or more basic groups in finely dispersed and/or dissolved form, wherein the active substance is soluble in oil and has a pKa of at least 7.5, the aqueous phase is set at an acid pH by containing a physiologically tolerated buffer system, and the disperse phase gives a positive zeta potential of at least +15 mV after dilution of the emulsion ready for administration to a fat content of 0.08% by weight.

The level of the positive zeta potential of the emulsion ready for administration is responsible for the stability of the emulsion, because only after a minimum positive charge has been reached on the interface are the repulsive forces so large that creaming or oil formation is prevented. The exact pH which must be set up in the aqueous phase in order to exceed the required limit of +15 mV depends not only on the basicity of the active substance, expressed by its pKa, but also to a certain extent on the concentration of the active substance in the composition, i.e. the higher the concentration, the lower the acidity required to reach the required positive charge in the disperse phase. Finally, the lecithin is also included, since the negative zeta potentials of lecithins can vary, depending on the purity, from −40 or −50 mV to near 0 (in the case of pure phosphatidylcholine), measured on a fat emulsion containing no active substance at pH 7.4.

Finally, the ion concentration which results in the aqueous phase by the interaction of all these factors is crucial while maintaining the solubility of the active substance in oil. In this connection it may be assumed that the value of +15 mV is the lower limit for stability of the composition.

A positive zeta potential of at least +30 mV is preferred, and one of at least +40 mV is particularly preferred, especially when the composition is to be autoclaved.

Besides the solubility in oil, it is also important that the hydrophobicity of the active substance is maximal, and it is necessarily true here too that a high hydrophobicity favors the formation of a high positive zeta potential but, at the same time, ensures that most of the active substance remains in the oil phase. It may be assumed that the hydrophobicity is high at a partition coefficient log P, measured in the octanol/water system, non-ionized, which is considerably higher than 2.5–3, the limit of 2.5–3 resulting from the detection limit for many active substances. Calculated values of log P should preferably exceed 4.

For a chosen active substance, it is advisable to determine by a preliminary test the pH at which a sufficiently high positive zeta potential is set up. It has emerged in practice that sufficiently high positive zeta potentials to obtain emulsions with excellent stability are usually achieved at pH values in the range 4–5.5, especially when the chosen active substance has a pKa of at least 8.

The chosen pH for strongly hydrophobic active substances with a pKa of 8–10 and an active substance content of 0.5–3% by weight is particularly preferably in the range 4–5.5, in which case the emulsion should contain 8–25% by weight of a vegetable oil and 1–2% by weight of a phospholipid as emulsifier.

A considerable reduction in the pH beyond that necessary to achieve the required zeta potential is not worthwhile and entails the risk of reducing the solubility of the base in oil too far. This may lead to reduced tolerability of the composition. As a rule, the acidity +should not be increased further after a zeta potential of 60 mV has been reached.

The required pH can be set up by using all buffer systems which are approved for pharmaceuticals for intravenous administration and which do not react with the active substance. Examples of such buffer systems are acetate/acetic acid buffer, phosphate buffer and citrate buffer. The fat component can be any conventional fat, especially oil, used for preparing fat emulsions intended for i.v. administration. Vegetable oils, such as soybean, peanut, safflower, olive, corn, rapeseed, coconut, sesame, sunflower, palm oil and the like, are preferred. The fat content is 5–30% by weight, expediently 8–25% by weight, preferably 10–20% by weight. It is advantageous to increase the fat content as the active substance content increases.

Phospholipids which may be mentioned are both the conventional egg phosphatides and soybean phosphatides, it being possible to use both those containing about 80% phosphatidylcholine and a certain proportion of acid impurities, which results in a negative zeta potential of −40 to −50 mV in a fat emulsion containing no active substance at pH 7.4, and more highly purified products which are 90% or more composed of one or more phosphatidylcholines. It is also possible to employ pure phosphatidylcholines which carry scarcely any negative charge. It is easiest using these to achieve high positive charges in the disperse phase. The nature of the chosen phospholipid must, as already mentioned, also be taken into account in the choice of the pH. Surprisingly, the effect of relatively large amounts of acid constituents in the emulsifier is considerably less at the acid pH values to be set up according to the invention than at neutral pH, so that even with conventional phospholipids which yield emulsions with a negative zeta potential of −40 to −50 mV without an active substance content at pH 7.4, it is possible usually to achieve sufficiently high positive zeta potentials, even exceeding +30 mV, at pH values below 6. The amount of phospholipid is expediently from 1 to 2% by weight. It is also possible, if desired, to use other conventional, especially non-ionic, emulsifiers together with the phospholipid.

Basic hydrophobic active substances which are suitable for producing the stable emulsions according to the invention are all those which, besides basicity, have pronounced hydrophobicity and are soluble in oil. Very favorable results are obtained with active substances belonging to the group of 5-(phenethylamino)-2-phenylvaleronitriles, with levemopamil being particular preferred. This active substance can be converted according to the invention into very stable and extremely well tolerated presentations based on a fat emulsion as carrier. These have no unpleasant side effects whatever on administration and, in this respect, are superior to aqueous presentations of this active substance. Very good results are also achieved with 2-dodecyl-5-(methyl-3-methoxyphenethylamino)- 2-(3-methoxyphenyl)valeronitrile (anipamil). Very good results are also achieved with active substances belonging to the group of neuroleptic phenothiazines with basic groups, particular attention being drawn to 10-(3-dimethylaminopropyl)phenothiazine with pKa 9.4 (promazine), 10-(2-dimethylaminopropyl)phenothiazine, pKa 9.1 (promethazine) and 4-{3-[2-(trifluoromethyl)phenothiazin- 10-yl]propyl}-1-piperazinoethanol, pKa 8.05 (fluphenazine). Finally, it is also possible to convert basic local anesthetics, such as tetracaine, into presentations according to the invention.

To produce the emulsions according to the invention, the oil, the active substance and the emulsifier are mixed into the aqueous phase which has already been set at the pH which is required, or has been determined by the preliminary test, by the buffer system. Preliminary emulsification of the mixture is followed by final treatment by multiple high-pressure homogenization which is continued until an average particle size of below 500 mm is reached. It is possible for the active substance first to be dissolved in the oil, after which the resulting mixture is introduced into a previously dispersed mixture of the phospholipid with the aqueous phase containing the buffer.

However, it is equally possible first to mix the active substance with the phospholipid, to disperse this mixture in the aqueous phase and subsequently to mix in the oil. It is possible to use conventional high-pressure homogenizers or microfluidizers for the high-pressure homogenization.

It is desirable in many cases to adjust the osmotic pressure to physiological conditions, especially when the emulsion according to the invention is to be administered intravenously. This adjustment can be carried out by adding a physiological non-ionic substance. Glycerol is preferred in this connection.

The zeta potential was determined in the following examples using a commercial apparatus (Zetasizer 3 supplied by Malvern), in which the microelectrophoresis is coupled to photon correlation spectroscopy based on a helium/neon laser. The evaluation was carried out by an on-line computer.

The drawing shows the change in the zeta potentials taking the example of levemopamil at various dilutions from 0.8 to 0.002 g/l or 0.08 to 0.0002% by weight of fat, which correspond to dilutions of from 1:250 to 1:10,000 starting from a 20% strength fat emulsion. The starting emulsions had various fat contents and/or active substance contents and were set at pH 5.

The plots are based on the following figures:

| Fat content | Active substance content | Zeta potentials in mV at g/l fat | | | | |
|---|---|---|---|---|---|---|
| | | 0.8 | 0.4 | 0.2 | 0.02 | 0.002 |
| 20% | 2% | 55.8 | 49.0 | 41.9 | −4.9 | −6.3 |
| 10% | 2% | 53.1 | 45.1 | 35.7 | −17.2 | −5.7 |
| 10% | 1% | 57.1 | 49.2 | 42.5 | −9.2 | −6.6 |
| 5% | 2% | 53.2 | 48.1 | 41.9 | −11.8 | −1.8 |
| 5% | 1% | 51.6 | 42.6 | 34.1 | −14.5 | −3.5 |
| 20% | 0.5% | 35.1 | 32.0 | 19.0 | −2.1 | −6.3 |

The low gradients obtained from 0.8 to 0.2 g/l fat underline the relevance of the values for the zeta potential found at 0.8 g/l fat or 0.08% by weight for the electrostatic conditions in the undiluted emulsion.

The emulsions according to the invention can be employed for all purposes for which liquid presentations of pharmaceutical active substances are used. They are particularly suitable for oral, nasal, pulmonary or vaginal administration. A particular advantage is that they are, by reason of their composition, not merely suitable for intravenous administration but in fact especially suited to this, and are very well tolerated.

EXAMPLE 1

12 g of OVOTHIN® 200 suitable for parenteral administration, which is more than 90% composed of phosphatidylcholine and gives a zeta potential of −20 mV as a fat emulsion without active substance in water at pH 7.4, were suspended in 725 ml of an acetate/acetic acid buffer solution (5 mmol/l), which had been set at pH 5, at 50°–60° C. and mixed with 23 g of 86% pure glycerol to adjust the osmotic pressure. The resulting aqueous mixture was then prehomogenized once under 200 bar. 20 g of levemopamil were dissolved, likewise at 50°–60° C., in 200 g of soybean oil; the resulting oil phase was dispersed in portions in the aqueous phase and emulsified once under 200 bar. After the pH had been readjusted to 5 by adding acetic acid, the complete mixture was homogenized 3 times under 200 bar. If larger particles were still detectable after this, these were reduced in size by a subsequent emulsification.

The resulting emulsion was left to cool to room temperature under a nitrogen atmosphere, filtered through a 5 µ filter and bottled. Sterilization at 121° C. for 15 minutes resulted in an emulsion with the following characteristics: zeta potential of a 250-fold dilution corresponding to a fat concentration of 0.08% +56 mV, average particle size 255 nm, active substance content 2 g/100 ml, which is 60 mmol/l.

Emulsions of pH 4 and pH 6 were produced in a similar manner.
Characteristics at pH 4: zeta potential+54 mV, particle size 210 nm, active substance concentration 2%
Characteristics at pH 6: zeta potential+37 mV, particle size 300 nm, active substance concentration 2%

EXAMPLE 2

20 g of anipamil in the form of the free base were mixed with 200 g of soybean oil. 12 g of OVOTHIN® 200 were dispersed as described in Example 1 with 725 ml of a sodium acetate/acetic acid buffer solution set at pH 5, mixed with the oil/active substance mixture and subjected to the high-pressure homogenization.

Sterilization in a rotary autoclave at 121° C. for 15 minutes resulted in an emulsion with the following values: zeta potential +54 mV, average particle size 300 nm, active substance content 2 g/100 ml, which is 60 mmol/l. Anipamil-containing emulsions with 2% active substance in 20% fat with pH values of 4 and 6 were obtained in an entirely corresponding manner.

The characteristics of these were as follows:
pH 4: average particle size 270 nm, zeta potential +56 mV, active substance content 2 g/100 ml
pH 6: average particle size 330 nm, zeta potential +41 mV, active substance content 2 g/100 ml

EXAMPLE 3

12 g of OVOTHIN® in 200 were suspended at 50°–60° C. in 825 ml of an aqueous sodium acetate/acetic acid buffer solution (5 mmol/l) set at pH 5 and subsequently 20 g of glycerol and then 20 g of levemopamil base were stirred in, after which the pH was returned to 5 by adding acetic acid. After prehomogenization, 100 g of soybean oil were introduced in portions and dispersed, after which the mixture was subjected to a high-pressure homogenization 3 times under 200 bar. Any larger particles still present were converted into smaller particles by subsequent homogenization. After cooling, the emulsion was autoclaved at 121° C. It then had the following characteristics:
zeta potential +53 mV, average particle size 230 nm, active substance content 2 g/100 ml, which is 60 mmol/l, fat content 10% by weight.

EXAMPLE 4

12 g of an egg lecithin containing 90% phosphatidylcholine, which gave a zeta potential of −20 mV at pH 7.4, (OVOTHIN® 200) and 20 g of glycerol were dispersed in 875 ml of a sodium acetate/acetic acid buffer solution set at pH 5 as described in Example 1, and, at 50°–60° C., a mixture of 20 g of levemopamil base and 50 g of soybean oil was added in portions. The mixture was homogenized first under 200 bar and, after correction of the pH, the homogenization was continued under 140 bar until the average particle size was 220 mm. After the bottling and sterilization carried out as in Example 1, the emulsion gave a zeta potential of +53 mV. The average particle size was 220 mm. The active substance content was 2 g/100 ml, which is 60 mmol/l, and the fat content was 5% by weight.

EXAMPLE 5

1 g of levemopamil base was mixed with 5 g of soybean oil. The mixture was added to a previously dispersed mixture of 1.2 g of a highly purified lecithin, 2 g of glycerol and 88 ml of a buffer solution set at pH 5, and was subjected to high-pressure homogenization with the pressure increasing from 140 to 200 bar. Sterilization in a rotary autoclave at 121° C. for 15 minutes resulted in an emulsion with the following values: zeta potential +52 mV, average particle size 230 nm, active substance content 1 g/100 ml corresponding to 30 mmol/l, fat content 5% by weight.

EXAMPLE 6

12 g of egg lecithin with a zeta potential of −20 mV were dispersed (Ultraturrax) in 730 ml of an acetic acid/acetate buffer solution (5 mmol/l) of pH 5 isotonisized with glycerol; 20 g of promethazine base were incorporated in this dispersion and then the resulting mixture was mixed with 200 g of soybean oil and emulsified 4 times in a high-pressure homogenizer under 200 bar. After 15 minutes in a rotary autoclave at 121° C., the emulsion had the following characteristics:
zeta potential +46 mV, average particle size 250 nm, active substance content 20 g/l, fat content 20% by weight.
Promethazine-containing emulsions of pH 4 and pH 6 were prepared in a corresponding manner.
Characteristics at pH 4: zeta potential +52 mV, average particle size 250 nm, active substance content 20 g/l
Characteristics at pH 6: zeta potential +41 mV, average particle size 280 nm, active substance content 20 g/l

EXAMPLE 7

2 g of promazine base were dispersed as described in Example 6 in 73 ml of buffer/glycerol solution of pH 5 which contained 1.2 g of the same egg lecithin as used in Example 6 with 20 g of soybean oil, and then subjected to high-pressure homogenization 4 times with the pressure increasing each time from 140 to 200 bar. After autoclaving a stable emulsion With the following characteristics was obtained: zeta potential +44 mV, average particle size 230 nm, active substance content 2%, fat content 20% by weight. The emulsions with pH 4 and pH 6 produced correspondingly had zeta potentials of +56 mV (pH 4) and +39 mV (pH 6) with the other characteristics the same.

EXAMPLE 8

10 g of levemopamil were dissolved in 100 g of soybean oil to prepare an emulsion. This mixture was dispersed with a high-speed stirrer at about 60° C. in 825 ml of an acetate buffer solution which was set at pH 5 and isotonisized with glycerol and which contained 12 g of OVOTHIN® 200, and was subjected to high-pressure homogenization in 4 steps under 200 bar.

Bottling and sterilization in a rotary autoclave at 121° C. for 15 min. resulted in an emulsion with the following characteristics:
zeta potential +57 mV, average particle size 300 nm, active substance content 10 g/l corresponding to 30 mmol/l, fat content 10% by weight.

EXAMPLE 9

20 g of levemopamil dissolved in 200 g of soybean oil were incorporated using a high-speed stirrer into 725 ml of an acetate buffer solution which was isotonisized with glycerol and set at pH 5 and which contained 12 g of an egg lecithin with a phosphatidylcholine content of 80% and a zeta potential at pH 7.4 of −40 to −50 mV (LYPOID E 80®), and subsequently subjected to high-pressure homogenization in 4 steps under 160–180 bar.

The emulsion produced in this way was filtered through 5μ filters, bottled and sterilized at 121° C. with rotation for 15 min. The following values were measured on the finished emulsion:
zeta potential +44 mV, average particle size 300 nm, active substance content 20 g/l, fat content 20% by weight.

We claim:

1. A stable emulsion which is suitable for pharmaceutical administration of the oil-in-water type, which contains in the lipid phase a hydrophobic pharmaceutical active substance, comprising
   a) a dispersed lipid phase formed by a vegetable oil, which is present in the emulsion in an amount of 5–30% by weight and is stabilized by a phospholipid as emulsifier, present in an amount of 0.5–2% by weight of the emulsion,
   b) the hydrophobic pharmaceutical active substance being present in said lipid phase, which is soluble in oil, sparingly soluble in water, strongly basic having a pKa of at least 8 and is present in the lipid phase in form of the base,
   c) an aqueous phase, which contains a physiologically tolerated buffer system, setting this aqueous phase at an acid pH and due to the low solubility in water a small amount of the active substance in ionized form,
whereby cations of said ionized form of the active substance formed in said acid aqueous phase confer a positive charge at the interface of the emulsion, giving a positive zeta potential of at least +30 mV after dilution of the emulsion ready for administration to a fat content of 0.08% by weight.

2. An emulsion as defined in claim 1, wherein the hydrophobic pharmaceutical active substance is selected from the group consisting of 5-(phenethylamino)-2-phenylvaleronitriles.

3. An emulsion as defined in claim 1, wherein the active substance is (−)-(S)-2-isopropyl-5-(N-methyl-phenethylamino)-2-phenylvaleronitrile.

4. An emulsion as defined in claim 1, wherein the active substance is 2-dodecyl-5-(N-methyl-3-methoxyphenethylamino)-2-(3-methoxyphenyl)valeronitrile.

5. An emulsion as defined in claim 1, wherein the active substance is selected from the group of neuroleptic phenothiazines with basic groups.

6. The composition of claim 1, suitable for intravenous administration.

7. An emulsion as defined in claim 1, which contains 8–25% by weight of the vegetable oil, 1–2% by weight of the phospholipid and 0.5–3% by weight of the hydrophobic pharmaceutical active substance and wherein the pH of the aqueous phase is adjusted to 4–5.5 by the buffer system.

* * * * *